(12) United States Patent
Palero et al.

(10) Patent No.: US 11,179,565 B2
(45) Date of Patent: Nov. 23, 2021

(54) NON-INVASIVE SKIN TREATMENT DEVICE USING R.F. ELECTRICAL CURRENT WITH A TREATMENT SETTINGS DETERMINER

(71) Applicant: KONINKLIJKE PHILIPS N.V., Eindhoven (NL)

(72) Inventors: Jonathan Alambra Palero, Eindhoven (NL); Ralph Timotheus Huijgen, Eindhoven (NL); Martin Jurna, Eindhoven (NL); Babu Varghese, Eindhoven (NL); Marco Baragona, Eindhoven (NL); Hendrik Halling Van Amerongen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 367 days.

(21) Appl. No.: 15/563,982

(22) PCT Filed: Mar. 29, 2016

(86) PCT No.: PCT/EP2016/056745
§ 371 (c)(1),
(2) Date: Oct. 3, 2017

(87) PCT Pub. No.: WO2016/162234
PCT Pub. Date: Oct. 13, 2016

(65) Prior Publication Data
US 2018/0133469 A1    May 17, 2018

(30) Foreign Application Priority Data
Apr. 8, 2015 (EP) .................................. 15162786

(51) Int. Cl.
*A61N 1/32* (2006.01)
*A61N 1/40* (2006.01)
(Continued)

(52) U.S. Cl.
CPC .............. *A61N 1/328* (2013.01); *A61N 1/06* (2013.01); *A61N 1/403* (2013.01); *A61B 2018/0047* (2013.01); *A61B 2018/0066* (2013.01)

(58) Field of Classification Search
CPC combination set(s) only.
See application file for complete search history.

(56) References Cited

U.S. PATENT DOCUMENTS 4,416,277 A * 11/1983 Newton ............. A61B 18/1233
128/908
6,413,255 B1    7/2002 Stern
(Continued)

FOREIGN PATENT DOCUMENTS

WO    2010098784 A1    9/2010
WO    2012023129 A1    2/2012
(Continued)

OTHER PUBLICATIONS

Stephen Mulholland, "Radio Frequency Energy for Non-Invasive and Minimally Invasive Skin Tightening", Clin Plastic Surg 38 (2011) 437-448.

*Primary Examiner* — Joseph A Stoklosa
*Assistant Examiner* — Adam J Avigan (57) ABSTRACT

The invention provides a non-invasive skin treatment device (100) comprising an r.f. treatment electrode (10); a return electrode (40); an r.f. generator (20) configured and arranged such that, during treatment, an r.f. treatment signal is applied between the r.f. treatment electrode (10) and the return electrode (40) for heating an inner region (15) of skin; an impedance measurement circuit (35) configured and arranged to measure, before treatment of the inner region, an initial skin impedance ($Z_o$) between the r.f. treatment electrode (10) and the return electrode (40); and a treatment
(Continued)

settings determiner (30) configured and arranged to determine, before treatment of the inner region (15), treatment settings associated with the r.f. treatment signal depending on the initial skin impedance ($Z_o$) and on a dimension of the r.f. treatment electrode (10) in the contact plane, the treatment settings comprising at least one of a treatment duration ($T_D$) associated with a desired treatment result, and an r.f. electrical parameter associated with the r.f. treatment signal. The skin treatment device (100) further comprises a controller (25) configured and arranged to consecutively activate the impedance measurement circuit (35) and the treatment settings determiner (30) before treatment of the inner region (15), configure the r.f. generator (20) to provide the r.f. treatment signal according to the treatment settings, and activate the r.f. generator (20) to apply the r.f. treatment signal to the inner region (15) for the treatment duration ($T_D$). The invention is based on the insight obtained from multiple measurements made during the creation of microscopic thermal lesions in an inner region of skin by applying r.f. measurement and treatment signals. By analyzing the histological and heating results, a relationship was obtained between the initial impedance ($Z_o$), the dimension of the r.f. treatment electrode (10), and the treatment settings required to obtain a particular skin treatment result. This relationship has been found to be relatively constant for different subjects, different treatment locations on the body and different skin moisture contents. The invention makes it possible to preset or predetermine, i.e. in advance, the treatment duration ($T_D$) and/or the r.f. electrical parameters associated with the r.f. treatment signal accurately enough to avoid undesired skin damage during the treatment. The device can be simpler, as it is no longer essential to continuously monitor the impedance during treatment to determine the onset of undesired skin damage, such as ablation, which is the safety feature known from conventional devices.

20 Claims, 5 Drawing Sheets

(51) Int. Cl.
*A61N 1/06* (2006.01)
*A61B 18/00* (2006.01)

(56) References Cited

U.S. PATENT DOCUMENTS

| | | | |
|---|---|---|---|
| 2002/0165531 A1* | 11/2002 | Goble | A61B 18/1445 606/40 |
| 2007/0173813 A1* | 7/2007 | Odom | A61B 18/1445 606/51 |
| 2008/0039831 A1* | 2/2008 | Odom | A61B 18/1445 606/34 |
| 2008/0082097 A1* | 4/2008 | McPherson | A61B 18/16 606/35 |
| 2008/0091182 A1 | 4/2008 | Mehta | |
| 2008/0200969 A1 | 8/2008 | Weber | |
| 2010/0210993 A1 | 8/2010 | Flyash | |
| 2010/0217255 A1* | 8/2010 | Greeley | A61B 18/18 606/33 |
| 2011/0015687 A1 | 1/2011 | Nebrigic | |
| 2012/0150168 A1 | 6/2012 | Adanny | |
| 2014/0207217 A1 | 7/2014 | Lischinsky | |
| 2014/0228834 A1 | 8/2014 | Adanny | |
| 2015/0126913 A1 | 5/2015 | Jurna | |

FOREIGN PATENT DOCUMENTS

| | | |
|---|---|---|
| WO | 2012110996 A2 | 8/2012 |
| WO | 2013076714 A1 | 5/2013 |
| WO | 2015040049 A1 | 3/2015 |

* cited by examiner

NON-INVASIVE SKIN TREATMENT DEVICE USING R.F. ELECTRICAL CURRENT WITH A TREATMENT SETTINGS DETERMINER

This application is the U.S. National Phase application under 35 U.S.C. § 371 of International Application No. PCT/EP2016/056745, filed on Mar. 29, 2016, which claims the benefit of International Application No. 15162786.6 filed on Apr. 8, 2015. These applications are hereby incorporated by reference herein.

FIELD OF THE INVENTION

The invention relates generally to a treatment device for skin, in particular to a non-invasive skin treatment device using radio-frequency (r.f.) electrical current.

BACKGROUND OF THE INVENTION

Various forms of electromagnetic radiation, particularly laser light beams, have been used for many years for a variety of therapeutic and non-therapeutic treatments of the skin, such as hair removal, skin rejuvenation to reduce wrinkles, and the treatment of conditions like acne, actinic keratosis, blemishes, scar tissue, discoloration, vascular lesions, cellulite and tattoo removal. Most of these treatments rely on photothermolysis, wherein a treatment location in the skin is targeted by the treatment radiation.

For example, to treat wrinkles, the dermis layer of the skin is damaged by heating (thermolysis) to induce a wound response, while minimizing damage to the epidermis layer of the skin. These microscopic photo-thermal lesions may be created by fractional non-ablative treatment using laser.

Radio-frequency (usually abbreviated as r.f.) energy has also been used for skin rejuvenation and skin tightening in both the professional and home-use aesthetic treatment devices market. Home-use devices are frequently used for non-therapeutic or cosmetic treatments. Compared to laser treatment devices, r.f. treatment devices have a substantially lower cost price and can provide larger-volume deep-tissue treatment. Additionally, r.f. energy dissipation does not rely on the absorption of light by chromophores, so that tissue pigmentation does not interfere with the delivery of energy. The advantages of r.f. treatments over laser treatments, and some embodiments of known r.f. treatment devices, are described in the article "Radio Frequency Energy for Non-invasive and Minimally Invasive Skin Tightening", by R. Stephen Mulholland, Clin Plastic Surg 38 (2011) 437-448.

The basic principle of r.f. energy delivery at the skin surface to skin tissue is that an alternating current is applied in a closed circuit with the skin. The r.f. energy is dissipated as thermal energy primarily due to intramolecular vibrations. A broad range of thermal effects may be produced, including:

epidermal and dermal bio-stimulation by heat, where the cellular components and molecular expressions in the epidermis and the dermis are up-regulated due to induction of heat shock proteins;

sub-epidermal tissue contraction, where the dermis is heated and thermally denatured;

coagulation of the epidermal cells and sub-epidermal collagen, where the epidermis and the dermis is heated sufficiently to induce cell necrosis and a wound response, but without causing ablation (non-ablative lesions);

ablation, where the dermis or epidermis is heated sufficiently to cause vaporization, which occurs at a skin temperature higher than 100 degrees C.

These effects may have different desired effects on the skin. Superficial skin damages are used for skin rejuvenation of the epidermis or to enhance the penetration of substances, while sub-epidermal tissue contraction is primarily used for skin tightening purposes and to stimulate new collagen synthesis.

Skin rejuvenation is generally achieved by intentionally heating an inner (or first) region of skin, proximate to the skin surface and the r.f. treatment electrode, to a temperature that is significantly above normal body temperature, typically to a temperature above 55 degrees C., so as to induce collagen denaturation and/or coagulation and/or full ablation of the epidermal skin tissue. This heating causes collagen and epidermal tissue re-modelling, resulting in a rejuvenated skin. To minimize downtime and side effects while maintaining sufficiently high efficacy levels, skin rejuvenation is often performed on a fractional area of the skin surface through the creation of distributed small lesions in inner regions of the skin close to the skin surface, typically 100-300 microns in size and usually by achieving a temperature of between 65-90 degrees C. An r.f. treatment device to generate a fractional pattern of such inner regions of the skin is disclosed in WO 2012/023129 A1.

Skin tightening is a non-ablative treatment based on thermolysis by heating an inner region of the skin, in particular the dermal skin layer. Typically, the target of the treatment is the dermis layer, which is at least 0.5 mm below the outer surface of the skin.

The thermal effects generated depend on the properties of the r.f. energy delivered, such as frequency, power, and duration, the treatment regime, the electrode configuration, such as size and inter-electrode distance, and the use of a conductive substance. An r.f. treatment of a certain condition may require more than one treatment to be performed at the same or proximal locations to generate the same, similar or different thermal effects.

To date, fractional skin treatments using r.f. energy are limited to professional use and are not considered suitable for home-use. A major reason is safety, because incorrect operation can result in undesired damage to the skin, which increases the healing time. Undesired ablative damage can easily occur, resulting in unnecessary pain for the person being treated. This is particularly challenging since the amount of RF energy deposited in the tissue depends on local tissue impedance, and since skin tissue has an inhomogeneous impedance distribution. This uncertainty relating to the skin impedance combined with the use of high current densities and voltages results in uncertainty relating to the achieved temperatures in the skin tissue during treatment.

U.S. Pat. No. 6,413,255 B1 discloses an apparatus to treat human skin by means of radio-frequency (RF) energy. The apparatus comprises a temperature and impedance feedback system used to control the delivery of the RF energy to the skin by the RF electrodes. The temperature of the skin tissue is measured by a temperature sensor. The skin impedance is calculated based on measurements of the current delivered through the RF electrodes and of the voltage between the RF electrodes. The delivery of the RF energy is interrupted when a maximum pre-set temperature or a set value of the impedance are exceeded. If the calculated impedance is within acceptable limits, RF energy continues to be applied to the skin.

WO 2015/040049 A1, KR-A-20120090007 and US 2011/0015687 A1 disclose similar examples of RF skin treatment devices comprising a sensor to measure the skin impedance during the application of the RF treatment energy, and comprising a controller to control the delivery of the RF treatment energy depending on the measured skin impedance.

SUMMARY OF THE INVENTION

An object of the invention is to improve a non-invasive skin treatment device using radio-frequency electrical current. In particular, an object of the invention is to provide an r.f. skin treatment device that provides better control over the heating during treatment.

According to the invention, the object is achieved by a non-invasive skin treatment device for heating an inner region of skin using radio-frequency (r.f.) electrical current, the skin treatment device comprising:

an r.f. treatment electrode, having a skin contact area defining a contact plane, configured and arranged to allow r.f. electrical current to pass through an outer surface of the skin and through the inner region;

a return electrode configured and arranged to allow r.f. electrical current to pass through the inner region and the outer surface of the skin;

an r.f. generator configured and arranged such that, during treatment, an r.f. treatment signal is applied between the r.f. treatment electrode and the return electrode through the inner region for heating the inner region;

an impedance measurement circuit configured and arranged to measure a skin impedance between the r.f. treatment electrode and the return electrode; and a treatment settings determiner configured and arranged to determine treatment settings associated with the r.f. treatment signal, wherein the skin treatment device further comprises a controller programmed such that, during operation, the controller, before activating the r.f. generator to apply the r.f. treatment signal, activates the impedance measurement circuit to measure an initial skin impedance ($Z_O$) between the r.f. treatment electrode and the return electrode, wherein the treatment settings determiner is programmed such that, during operation, the treatment settings determiner determines the treatment settings depending on the measured initial skin impedance ($Z_O$) and on a dimension of the r.f. treatment electrode in the contact plane, the treatment settings comprising at least the following:

a treatment duration ($T_D$) associated with a desired treatment result; and an r.f. electrical parameter associated with the r.f. treatment signal; and wherein the controller is further programmed such that, after activating the impedance measurement circuit to measure the initial skin impedance, the controller consecutively:

activates the treatment settings determiner to determine the treatment settings before activating the r.f. generator to apply the r.f. treatment signal;

configures the r.f. generator to provide the r.f. treatment signal according to the treatment settings; and activates the r.f. generator to apply the r.f. treatment signal to the inner region for the treatment duration ($T_D$).

The invention is based on the insight obtained from multiple measurements made during the creation of microscopic thermal lesions in an inner region of skin by applying measurement signals and r.f. treatment signals. Before the treatment, the initial skin impedance ($Z_O$) was measured using the measurement signal. During the experiments, the degree of heating in the inner region of skin was monitored to determine the onset of coagulation following a heating phase. The onset of ablation was also determined following the coagulation phase. By analyzing the histological and heating results, a relationship was obtained between the measured initial impedance ($Z_O$), the dimensions of the r.f. treatment electrode, and r.f. treatment settings associated with the r.f. treatment signal, comprising at least the treatment duration and an r.f. electrical parameter associated with the r.f. treatment signal. Said relationship has been found to be relatively constant for different subjects, different treatment locations on the body and different skin moisture contents. The invention therefore makes it possible to determine in advance, i.e. before the actual treatment, the appropriate r.f. treatment settings accurately enough to avoid undesired skin damage during the treatment, because the treatment duration ($T_D$) and the r.f. electrical parameter are either accurately preset before treatment or predetermined accurately. By virtue thereof, the device can be simpler, because it is no longer required to continuously monitor the skin impedance during treatment to determine the onset of an undesired treatment result, such as coagulation or ablation, which is the safety feature known from conventional r.f. skin treatment devices. This onset of an undesired treatment result may be considered to be associated with the maximum treatment duration required to achieve the desired treatment result. The treatment settings may be determined so as to take into account other effects, such as treatment efficacy and/or subject discomfort.

It may be advantageous to associate the treatment duration ($T_D$) with a transition in the inner region from a desired treatment result to an undesired treatment result.

Typically, for skin treatment, it is desired to finish the treatment in as few treatment sessions as possible. By associating the treatment duration with the transition from a desired treatment result to an undesired treatment result, the treatment duration is effectively used without causing undesired skin damage. For treatments where only heating of the skin is desired, the undesired treatment result is associated with tissue coagulation within the inner region. For treatments where only tissue coagulation is desired, the undesired treatment result is associated with tissue ablation within the inner region.

In a preferred embodiment of the skin treatment device according to the invention, a maximum dimension of the r.f. treatment electrode in the contact plane of the r.f. treatment electrode is less than or equal to 2 mm.

The depth of the lesion is limited by the dispersion of the electric r.f. field lines in the inner skin region extending from the r.f. treatment electrode to the return electrode. With smaller-dimensioned r.f. treatment electrodes, also referred to as micro-electrodes, the region being heated is localized in the skin tissue region immediately below the micro-electrode where the electric r.f. field lines are most dense. It is in this region that the skin is heated most intensely, or where the skin is damaged and lesions are created.

In a preferred embodiment of the skin treatment device according to the invention, the treatment settings determiner is programmed such that the treatment settings determiner determines the treatment settings according to the following formula:

$$J = K \cdot R \cdot TT \cdot P_M \cdot (1 - \exp(-T_D/TT)),$$

wherein:

J is a skin damage onset factor associated with a transition from a desired treatment result to an undesired treatment result;

K is a constant, per millimeter-millijoule, dependent on skin tissue thermal and dielectric properties;

R is a radius of the r.f. treatment electrode in the contact plane in millimeters;

TT is a thermal time constant of skin tissue in milliseconds;

$P_M$ is an r.f. power associated with the r.f. treatment signal in watts, equal to $V_M^2/Z_O$, wherein $V_M$ is the voltage of the r.f. treatment signal; and $T_D$ is the treatment duration in milliseconds.

The inventors were the first to establish a predictable relationship between a measured initial skin impedance ($Z_O$), a radius of the r.f. treatment electrode, and the treatment settings associated with the r.f. treatment signal, allowing the treatment settings associated with the r.f. treatment signal to be determined accurately enough before the actual treatment, such that further skin impedance measurements during the actual treatment to determine or correct the treatment settings are no longer essential to provide the desired treatment result.

In a preferred embodiment of the skin treatment device according to the invention, said constant K is equal to $0.38\pm0.03$ mm$^{-1}$ mJ$^{-1}$. In another preferred embodiment of the skin treatment device according to the invention, said thermal time constant TT is equal to $40.4\pm4.8$ milliseconds. These constants were derived from the measurements made by the inventors, and have been found to provide results which are sufficiently repeatable and sufficiently accurate.

In a preferred embodiment of the skin treatment device according to the invention, said skin damage onset factor J is one or more of the following:

$J=1\pm0.3$, when a transition within the inner region from a desired treatment result to an undesired treatment result is associated with onset of non-ablative coagulation damage; or $J=1.7\pm0.5$, when a transition within the inner region from a desired treatment result to an undesired treatment result is associated with onset of ablative damage.

The onset factor J allows the treatment result of the device to be preset or predetermined. Setting J equal to approximately 1 will result in the onset of non-ablative coagulation damage, which is also the end of the heating treatment regime. Setting J equal to approximately 1.7 will result in the onset of ablative damage, which is also the end of the non-ablative coagulation treatment regime.

In a preferred embodiment of the skin treatment device according to the invention, the r.f. electrical parameter associated with the r.f. treatment signal is one or more of the following:

$I_M$, being an electrical current of the r.f. treatment signal in Amperes;

$V_M$, being a voltage of the r.f. treatment signal in Volts; and $P_M$, being a power associated with the r.f. treatment signal in Watts.

The r.f. power $P_M$ in Watts may be determined according to one or more of the following formulas:

$$P_M = I_M^2 \cdot Z_O, \text{ or}$$

$$P_M = V_M^2/Z_O,$$

wherein:

$I_M$ is the electrical current of the r.f. treatment signal in Amperes;

$Z_O$ is the initial skin impedance in Ohms measured by the impedance measurement circuit; and $V_M$ is the voltage of the r.f. treatment signal in Volts.

In a preferred embodiment of the skin treatment device according to the invention, the controller is further programmed such that the controller prevents the r.f. generator from being activated to apply the treatment signal to the inner region if the measured initial skin impedance is greater than a predetermined upper limit or smaller than a predetermined lower limit. In this embodiment, as an additional safety feature, the r.f. treatment signal is prevented from being applied to the skin if the measured initial skin impedance is too high or too low. For example, too high a skin impedance may be the result of poor electrical contact between one of the electrodes and the skin. Too low a skin impedance may be the result of the presence of a highly conductive material between the electrodes. In both cases, the r.f. treatment signal may be blocked by, for example, turning off the r.f. generator or inserting a barrier between the skin and the r.f. treatment electrode.

In a preferred embodiment of the skin treatment device according to the invention, the impedance measurement circuit is further configured and arranged to measure, during treatment, an actual skin impedance between the r.f. treatment electrode and the return electrode, and the controller is further programmed such that the controller interrupts, during treatment, the r.f. generator to prevent it from applying the r.f. treatment signal to the inner region if the actual skin impedance is greater than a predetermined further upper limit or smaller than a predetermined further lower limit.

Although actual skin impedance measurement during treatment is not essential when using the present invention, it may be advantageous to optionally do this. As an additional safety factor, this may be used to interrupt treatment due to an unexpected skin impedance value.

The treatment device according to the invention may be advantageously used in the treatment of skin conditions, in particular wrinkles, fine lines, laxity, sagging skin, acne, actinic keratosis, blemishes, scar tissue or discoloration. Many of these conditions are treated in non-therapeutic or cosmetic treatments.

It should be noted that items, which have the same reference numbers in different Figures, have the same structural features and the same functions, or represent similar signals. Where the function and/or structure of such an item has been explained, there is no necessity for repeated explanation thereof in the detailed description.

DETAILED DESCRIPTION OF THE EMBODIMENTS

Figure 1:
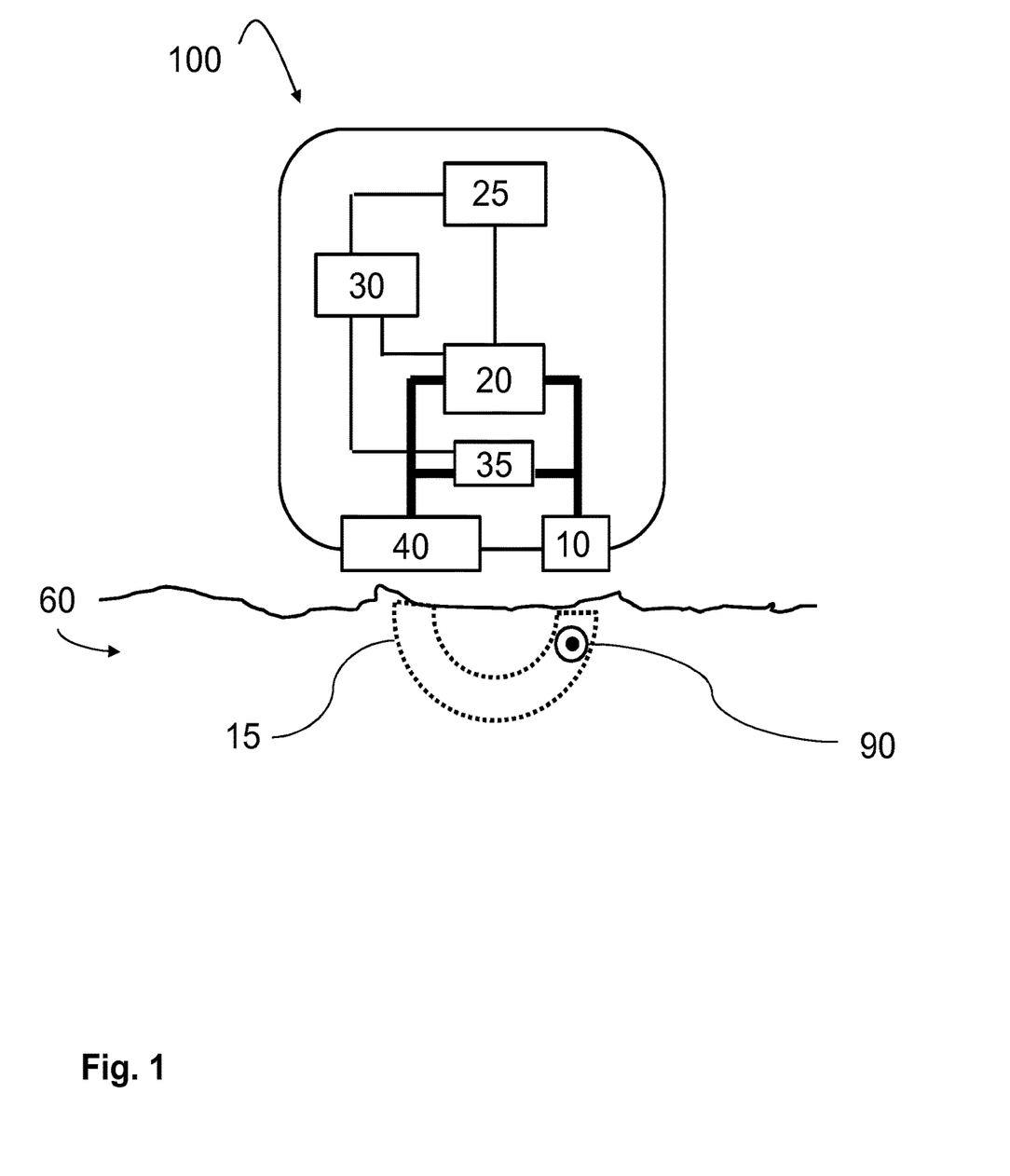
FIG. 1 diagrammatically shows an embodiment of a non-invasive skin treatment device according to the invention in use when treating skin.

FIG. 1 schematically shows an embodiment of a non-invasive skin treatment device 100 comprising an r.f. treatment electrode 10 and a return electrode 40, each of which have an electrical skin contact area. The device 100 further comprises an r.f. generator 20 configured and arranged to be operated in bipolar mode by being electrically connected to the r.f. treatment electrode 10 and the return electrode 40. The r.f. treatment electrode 10 is configured and arranged to allow r.f. electrical current to pass through an outer surface of the skin and through the inner region 15, and the return electrode 40 is configured and arranged to allow r.f. electrical current to pass through both the inner region 15 and an outer surface of skin.

The device 100 further comprises a controller 25, electrically connected to the r.f. generator 20, and programmed such that the controller 25 activates the r.f. generator before treatment to produce an r.f. measurement signal, and during treatment to produce an r.f. treatment signal. The r.f. treatment electrode 10 may extend between 0.1 mm to 1 mm in the contact plane defined by the skin contact area, and the return electrode 40 is preferably at least ten times larger in surface area to avoid heating below the return electrode 40, and to concentrate the heating in the skin region immediately below the r.f. treatment electrode 10.

The r.f. treatment signal selected depends on, inter alia, the type of treatment to be performed, the electrode geometries and dimensions and the depth of the inner region below the outer layer of skin. For example:

a fixed voltage, current or power for a particular duration, or a varying voltage, current or power, for a particular duration, or a combination of these.

For example, an AC waveform may be used, with a frequency in the range 0.3-100 MHz and a power in the range 1-400 W. A typical frequency used is 0.5-1 MHz, with a power in the range of 1-20 W.

The device 100 is configured and arranged to be brought into close proximity to human or animal skin 60, with the treatment electrode 10 and the return electrode 40 facing the outer layer of the skin. Each electrode comprises a skin contact area, which provides electrical contact with the skin 60 during use of that electrode. The treatment and return electrodes may make physical contact with the outer layer of skin, or they may be disposed such that there is a small gap with respect to the skin. Optionally, a conductive substance, such as a gel, may be used in this gap between the skin and the skin contact area to reduce any contact impedance between electrodes and the outer layer of skin.

The skin contact surface of the electrodes 10, 40 may be comprised in the same plane, or the skin contact surfaces may protrude, or may be recessed, with respect to each other. As the device 100 may need to be moved over the skin before, during or after use, substantially flat skin contact surfaces are preferred.

Within the inner region 15 of skin, a treatment target 90 is selected as the location where the heating is to be controlled. The position and depth of the treatment target 90 is determined, inter alia, by the arrangement and configuration of the treatment 10 and return 40 electrode configurations, and the ratio of the electrical skin contact areas of these electrodes. For example, the electrical skin contact area of the return electrode 40 may be 5 or more times greater than the electrical skin contact area of the r.f. treatment electrode 10. This ratio is predetermined and/or controlled to provide r.f. heating proximate the r.f. treatment electrode 10 in the inner region 15 at the treatment target 90. Increasing the electrical skin contact area of the return electrode 40 compared to the electrical skin contact area of the r.f. electrode 10, will increase the proximity of the treatment target 90 to the r.f. treatment electrode 10. The treatment target 90 may be disposed, inter alia, in the epidermis or dermis of the skin.

The r.f. treatment electrode 10 may be circular, annular, oval or rectangular in a cross-section comprised in the electrical skin contact area. For example, the r.f. treatment electrode 10 may be circular in a cross-section through the electrical skin contact area. The electrical skin contact area is proximate and approximately parallel to an outer layer of skin 60 during use. If the r.f. treatment electrode 10 has a diameter of 0.5 mm in that cross-section, and the distance, in the plane of the contact areas of the electrodes 10, 40, between the electrodes is 1 mm, then a typical voltage of the r.f. treatment signal may be 15-60V. Treatment duration is then typically less than 1 second, in a single pulse or multiple pulses. Micro-electrodes, having a diameter of 0.2-0.4 mm in cross-section, are particularly advantageous due to the very proximate treatment target 90.

The return electrode 40 may also be circular, annular, oval or rectangular in a cross-section comprised in the electrical skin contact area.

The treatment device 100 further comprises an impedance measurement circuit 35 configured and arranged to measure a skin impedance between the r.f. treatment electrode 10 and the return electrode 40. The measurement circuit 35 may be electrically connected to the r.f. treatment electrode 10 and the return electrode 40, or to separate impedance measurement electrodes, or to a combination of treatment and separate measurement electrodes The controller 25 is programmed such that, during operation, the controller 25, before activating the r.f. generator 20 to apply the r.f. treatment signal, activates the impedance measurement circuit 35 to measure an initial skin impedance $Z_O$ between the r.f. treatment electrode 10 and the return electrode 40.

In this embodiment, the r.f. generator 20 is controlled by the controller 25 such that, before treatment, an r.f. measurement signal is applied between the r.f. treatment electrode 10 and the return electrode 40 through the skin for impedance measurement. The controller 25 is further programmed such that the controller 25 activates the r.f. generator 20 before treatment to produce the r.f. measurement signal. It will be obvious to the skilled person that two different r.f. generators may also be used, i.e. one to generate the r.f. measurement signal and the other to generate the r.f. treatment signal. It will further be obvious to the skilled person that the measurement signal does not need to be an r.f. signal, but may be e.g. a DC measurement signal.

The r.f. measurement signal may have any suitable voltage, current, frequency and duration. The r.f. measurement signal is configured and arranged to avoid heating of the inner region 15 of the skin by more than a few degrees Centigrade during the measurement, preferably less than 1 degree Centigrade. This improves the accuracy of the impedance measurement.

For example, a short low-voltage r.f. pulse with a voltage in the range of 15-25 volts (rms), and a pulse duration in the range of 50-100 ms, such as one of 65 ms pulse duration and 20 volts (rms). Alternatively, more than one r.f. measurement pulse could be delivered to the skin, and an average of the impedances measured during all the measurement pulses may be used as the initial skin impedance ($Z_O$).

The frequency of the r.f. measurement signal may be 0.3-100 MHz, and typically the frequency used is 0.5-1 MHz. The frequencies of the r.f. treatment signal and the r.f. measurement signal are preferably similar to limit inaccuracies of the treatment settings determiner 30. However, it is not required that the frequencies of the r.f. treatment signal and the r.f. measurement signal are identical.

Although it is convenient to use the same set of electrodes for both the r.f. measurement signal and the r.f. treatment signal, this is not required. One or more separate electrodes may be used for the r.f. measurement signal, the impedance measurement circuit and the measurement electrodes being configured and arranged to measure as closely as possible the impedance of the skin tissue which is to be treated with the r.f. treatment signal. The accuracy of the treatment settings determiner 30 may be improved by using the same electrodes, as this may provide the highest degree of coincidence between the path of the r.f. measurement signal and the path of the r.f. treatment signal through the skin tissue.

The initial skin impedance ($Z_O$) may depend on, inter alia, the electrode configuration and separation, the anatomy of the treatment site, the local skin tissue moisture content, and the use of contact gel. For example, when using an r.f. treatment microelectrode 10 with a cross-section diameter comprised in the electrical skin contact area of 0.2 mm, a ring-shaped return electrode 40 surrounding the r.f. treatment electrode in the plane of the electrical skin contact areas, the ring having an inner diameter of 3 mm, and a contact gel, impedance values of 2000-10000 Ohms may be measured.

The treatment device 100 further comprises a treatment settings determiner 30 programmed such that, during operation, the treatment settings determiner 30 determines treatment settings, associated with the r.f. treatment signal, depending on the initial skin impedance $Z_O$ and on a dimension of the r.f. treatment electrode 10. The controller is further programmed such that, after activating the impedance measurement circuit to measure the initial skin impedance, the controller activates the treatment settings determiner to determine the treatment settings before activating the r.f. generator to apply the r.f. treatment signal. The treatment settings comprise at least the following:
 a treatment duration ($T_D$) associated with a desired treatment result; and
 an r.f. electrical parameter associated with the r.f. treatment signal.

The r.f. electrical parameter may be:
 $I_M$, being an electrical current of the r.f. treatment signal in Amperes (such as rms), or
 $V_M$, being a voltage of the r.f. treatment signal in Volts (such as rms).

It may also be an r.f. power ($P_M$) associated with the r.f. treatment signal. Any suitable power value may be used. Preferably, the r.f. power ($P_M$) is associated with the dissipated power in the skin. For example:
 if the r.f. generator is current-controlled, the treatment settings determiner 30 may be configured to determine the r.f. power ($P_M$) according to $P_M = I_M^2 \cdot Z_O$, where $Z_O$ is the initial skin impedance in Ohms measured by the impedance measurement circuit 35 and $I_M$ is the electrical current of the r.f. treatment signal in Amperes (such as rms);
 if the r.f. generator is voltage-controlled, the treatment settings determiner 30 may be configured to determine the r.f. power ($P_M$) according to $P_M = V_M^2/Z_O$, where $V_M$ is the voltage of the r.f. treatment signal in Volts (such as rms);
 If the r.f. generator is power-controlled, the treatment settings determiner 30 may be configured to determine an r.f. power ($P_M$) directly (such as rms).

For example, given a preset dimension of the r.f. treatment electrode 10 and a preset r.f. electrical parameter, the treatment duration $T_D$ may be determined by the treatment settings determiner 30. In a further example, given a preset treatment duration $T_D$ and a preset dimension of the r.f. treatment electrode 10, the r.f. electrical parameter may be predetermined. In a still further example, given a preset treatment duration $T_D$ and a preset r.f. electrical parameter, the required dimension of the treatment electrode 10 may be predetermined.

During operation, the treatment device 100 is brought into close proximity to human or animal skin 60, with the treatment electrode 10 and the return electrode 40 facing the outer layer of the skin.

Either automatically or following a command by the user, the controller 25 activates the r.f. generator 20 to produce an r.f. measurement signal between the r.f. treatment electrode 10 and the return electrode 40 through the skin for initial skin impedance ($Z_O$) measurement. Preferably, the path followed through the skin by the measurement signal will coincide to a high degree with the path to be followed by the subsequent r.f. treatment signal within the inner region 15. It may be advantageous, for achieving a sufficiently high coincidence, that the measurement signal passes through the treatment target 90, proximate the r.f. treatment electrode 10.

Either automatically or following a command by the user, the controller subsequently activates the treatment settings determiner 30 to determine the treatment settings, which includes setting or predetermining the treatment duration ($T_D$).

Either automatically or following a command by the user, the controller 25 subsequently configures and activates the r.f. generator 20 to produce an r.f. treatment signal between the r.f. treatment electrode 10 and the return electrode 40 through the inner region 15 of skin and through the treatment target 90. This is the start of the actual treatment.

The r.f. treatment signal is configured according to the treatment settings to dissipate the r.f. energy into the inner region 15 until the treatment duration ($T_D$) has been reached. At that point in time, the controller 25 deactivates the r.f. generator 20, the device 100 stops emitting the r.f. treatment signal, and the treatment ends before the heating in the inner region 15 causes undesired skin damage.

The r.f. electrical parameter, such as power ($P_M$), associated with the r.f. treatment signal may be used during the treatment to determine the energy dissipated in the inner region 15 of skin. The r.f. electrical parameter is preset or predetermined before treatment, based, inter alia, upon:
 the stage in a series of multiple stage treatments;
 the depth under the outer layer of skin where the treatment target 90 is disposed, and
 the electrode dimensions, geometries and separation.

In addition, factors such as discomfort and pain threshold of the subject may be taken into account, as well as limitations in the construction and components of the device used.

The inventors were the first to establish a predictable relationship between an initial skin impedance measurement ($Z_O$), the dimension of the r.f. treatment electrode 10, and the treatment settings associated with the r.f. treatment signal, allowing the treatment duration ($T_D$) to be preset or predetermined accurately enough before the actual treatment such that further skin impedance measurements during the actual treatment to determine the treatment result, for example continuous skin impedance measurements, are not essential.

R.f. treatment heads that are calibrated before treatment are known, for example from US 2012/0150168. However, these treatment heads do not set or predetermine the treatment duration before treatment. They continuously measure skin impedance to control the power delivered to the skin. Once a rise in skin impedance is detected during treatment, a fixed amount of energy is delivered to the skin or an amount that takes into account the energy already delivered. In other words, treatment settings are determined during treatment.

The r.f. treatment device of US 2012/0150168 also differs in its use of a multiplicity of r.f. treatment electrodes (64 in FIG. 1), and is operated at very high voltage and power values, i.e. 850 Vp-p and 50-400 mA, as the desired treatment result is ablation.

In a preferred embodiment, the treatment settings determiner 30 is programmed such that the treatment settings determiner determines the treatment settings according to the following formula:

$$J = K \cdot R \cdot TT \cdot P_M (1 - \exp(-T_D/TT)),$$

wherein:
  J is a skin damage onset factor associated with a transition between a desired treatment result and an undesired treatment result;
  K is a constant, per millimeter-millijoule, dependent on skin tissue thermal and dielectric properties;
  R is a radius of the r.f. treatment electrode 10 in the contact plane in millimeters;
  TT is a thermal time constant of skin tissue in milliseconds;
  $P_M$ is the r.f. power associated with the r.f. treatment signal in Watts; and
  $T_D$ is the treatment duration in milliseconds.

The skin damage onset factor J is preset or predetermined before the actual treatment, and is associated with a transition between the desired treatment result and an undesired treatment result within the inner region 15. For example, a value of $J=1\pm0.3$ is associated with the onset of non-ablative coagulation damage within the inner region, wherein the desired treatment result is heating of the inner region 15 without tissue damage. A value of $J=1.7\pm0.5$ is associated with the onset of ablative damage within the inner region 15, wherein the desired treatment result is non-ablative skin tissue coagulation. These values have been determined experimentally based on the transitions in the heating profile from the desired treatment result to the undesired treatment result. When these values are used, the treatment target 90 will be subjected to the maximum possible amount of heating without causing an undesired treatment result or entering the undesired treatment regime. This may reduce the total number of treatments required. To provide a higher degree of safety, a lower value of J may be used.

The invention is based on the insight obtained from multiple measurements made during the creation of microscopic thermal lesions in an inner region of skin by applying r.f. measurement and treatment signals.

Figure 3:
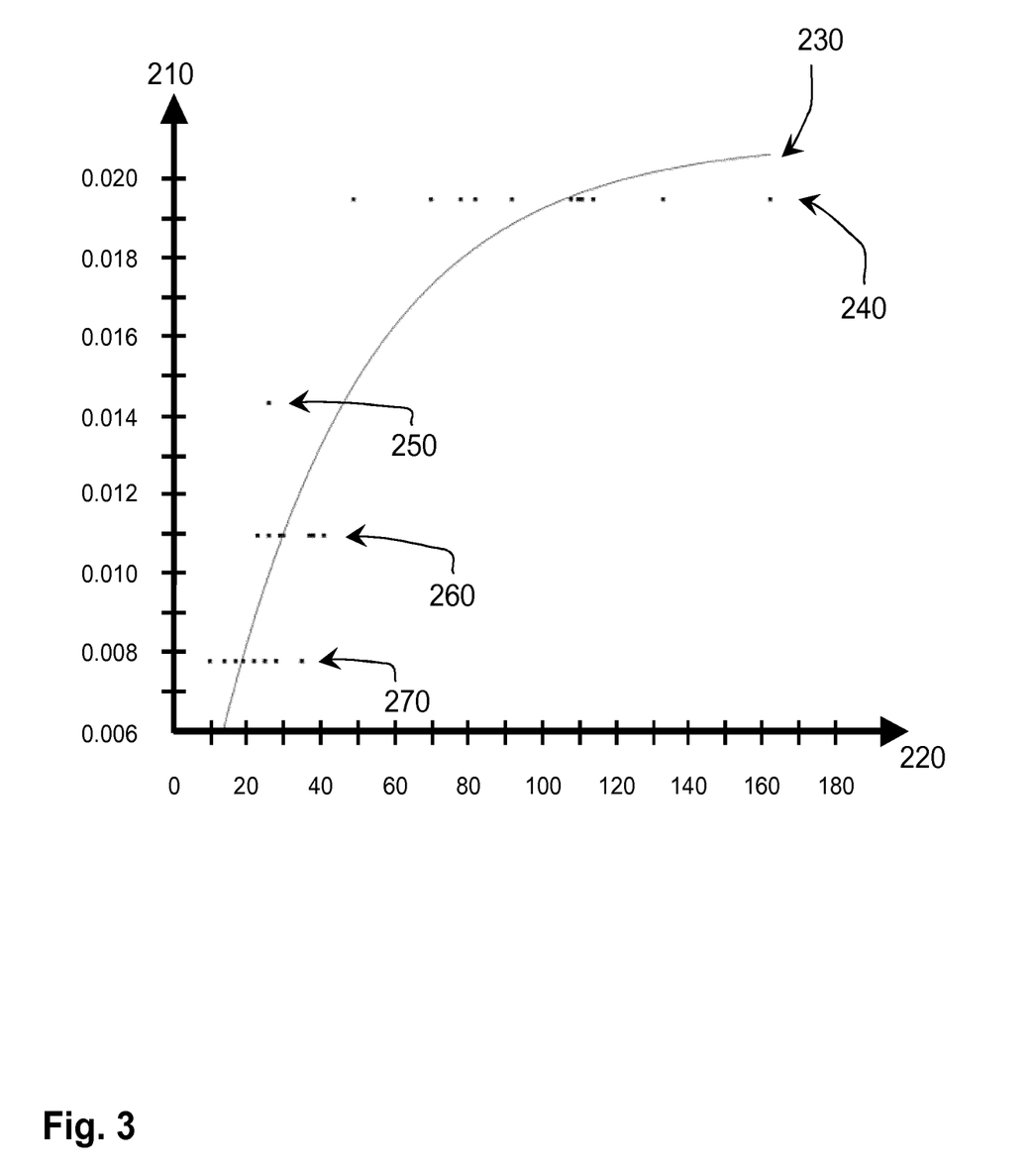
FIG. 3 depicts initial measurement data and a curve fitted to the initial measurement data to establish a relationship between a temperature change of 70 degrees C. and the local heating at a treatment target.

FIG. 3 shows initial measurement data 230, 250, 260, 270 and a curve 230 fitted to these data to establish a relationship between a temperature change of 70 degrees C., i.e. from 30 degrees C. to the vaporization or tissue ablation temperature of 100 degrees C., and the local heating at a treatment target. The horizontal axis 220 represents the treatment duration ($T_D$) until the onset of skin ablation from 0 to 180 milliseconds (ms), and the vertical axis 210 represents $70/V_M^2$ from 0.006 to 0.020 in steps of 0.001 degrees C. per Volt.

During the multiple measurements, fractional r.f. treatment was carried out on two ex vivo human skin samples, using a non-invasive treatment device comprising an r.f. treatment electrode 10 with a diameter of 200 micrometers surrounded by an annular return electrode having an inner radius of 3 mm in the plane of the skin contact areas of the electrodes. The voltage of the r.f. treatment signal ($V_M$) was set to either 60V, 70V, 80V or 95V.

Figure 2:
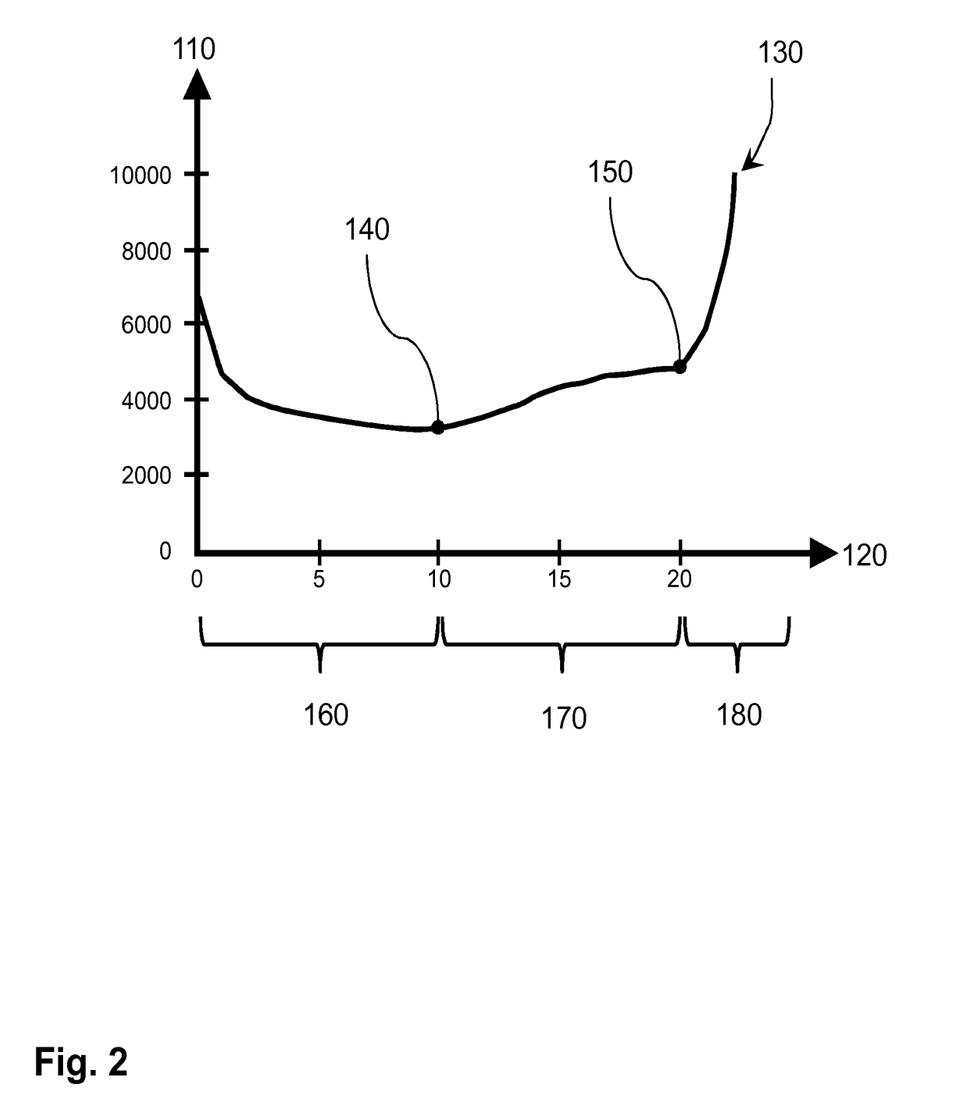
FIG. 2 depicts different treatment regimes based on changes in measured skin impedance during treatment.

The initial skin impedance $Z_0$, and treatment duration ($T_D$) until the onset of skin ablation were recorded. For determining the onset of skin ablation, it was convenient to use a real-time impedance monitoring system during these measurements to establish the transition (as depicted in FIG. 2 as point 150) from the coagulation treatment regime to the ablation treatment regime. Although this continuous impedance measurement system was used for these initial measurements, the relationship determined from the data causes such impedance measurement to be no longer required when actually treating skin with a device according to the invention.

FIG. 2 depicts the different treatment regimes based on the change in skin impedance during measurement. The horizontal axis 120 represents the r.f. treatment duration ($T_D$) in milliseconds, from 0 to 25 milliseconds. The vertical axis 110 represents the skin impedance measured during r.f. treatment in Ohms, from 0 to 10,000 Ohms. The impedance profile 130 during treatment was determined during the multiple measurements, and shows three sections:

a non-linear decay from the initial impedance (at 0 milliseconds) of approximately 6700 Ohm to approximately 3300 Ohms at 5 milliseconds. In this treatment regime 160 the skin is heated. This section starts at the beginning of the treatment and ends at the transition 140 from the heating regime 160 to the coagulation regime 170. During treatment, the skin tissue heats up, and it is known to the skilled person that the impedance decreases with increasing temperature. Due to tissue heat diffusion, the rate of increase in temperature results in a non-linear decay in impedance. The end of this treatment regime is at the approximately lowest point in the curve where the rate of change of impedance (dZ/dt) is approximately zero.

A slight increase in impedance from approximately 3300 Ohms at 5 milliseconds to approximately 4800 Ohms at 20 milliseconds. In this treatment regime 170 coagulation lesions are formed in the skin. This section starts at the transition 140 from the heating regime 160 to the coagulation regime 170 and ends at the transition 150 from the coagulation regime 170 to the ablation regime 180. As the r.f. treatment signal further heats up the skin tissue, thermally-induced physical changes occur in the tissue from protein denaturation or coagulation accompanied by local tissue contraction and/or short-lived formation of microbubbles in the intercellular and intracellular spaces, resulting in reversible formation of desiccated or dried-out tissue regions. These events contribute to a transient low-amplitude increase in the local impedance of the skin tissue.

An abrupt increase in impedance from approximately 4800 Ohms at 20 milliseconds to approximately 10,000 Ohms at 22.5 milliseconds, followed by an almost vertical increase of the impedance take place. In this treatment regime 180 ablation lesions are formed in the skin. This section starts at the transition 150 from the coagulation regime 170 to the ablation regime 180. When the r.f. treatment signal delivers sufficient energy to bring the local tissue temperature to the water vaporization temperature of 100° C., explosive ablation of the upper layers of the tissue occurs resulting in poor electrical contact between the tissue and the electrode. This accounts for the abrupt increase of the local impedance to very high values.

The distinct treatment regimes of FIG. 2 may be individually observable within the impedance signal due to the relatively small dimensions of the r.f. treatment electrode, which result in a more localized sampling area. The use of much larger electrode dimensions may not reveal these sections in the impedance signal due to the blending of the skin effects over a larger area. Without wishing to be bound by a specific theory, it is believed that the most critical dimension may be the maximum dimension of the r.f. treatment electrode in the contact plane, wherein the contact plane is defined by the electrode-skin contact area.

With respect to the one hundred r.f. treatments applied, thirty-one ablation events were detected using the real-time impedance measurement.

Without wishing to be bound by a specific theory, the temperature at a treatment target for localized heating in skin, when using a small electromagnetic energy source such as the r.f. treatment signal, is given by equation 1:

$$T(t) = C_0 \cdot TT \cdot V_M^2 \cdot (1 - \exp(-t/TT)),$$

wherein:
  T is the temperature in degrees C. at time t (in milliseconds) during the treatment
  Co is a constant, dependent on skin tissue thermal properties;
  TT is a thermal time constant of skin tissue in milliseconds;
  $V_M$ is the voltage associated with the r.f. treatment signal in Volts, and $V_M^2$ is equal to the power dissipated $P_M$ in Watts×the initial skin impedance Zo in Ohms; and
  t is the time during the treatment (in milliseconds) when the temperature T is determined.

It is assumed that the ablation onset occurs when water in the skin starts to vaporize at 100° C. Accordingly, the onset of ablation occurs when the skin, starting at approximately 30 degrees C., is heated with a sufficiently long r.f. treatment signal up to 100 degrees C. Accordingly, at the temperature change point of 70 degrees C., equation 1 may be applied as a fitting model for the data measurements using equation 2:

$$70 \text{ degrees C.}/V_M^2 = C_0 \cdot TT \cdot (1 - \exp(-T_A/TT)),$$

wherein:
  70 degrees C. is the temperature change associated with the onset of ablation;
  $V_M$ is the voltage associated with the r.f. treatment signal in Volts, and $V_M^2$ is equal to the power dissipated $P_M$ in Watts×the initial skin impedance Zo in Ohms;
  Co is a constant;
  TT is a thermal time constant of skin tissue in milliseconds; and
  $T_A$ is the amount of time (in milliseconds) that passes before the ablation temperature of 100 degrees C. is reached (assuming that the skin is initially at 30 degrees C.).

FIG. 3 depicts the thirty-one measurements made before the ablation temperature was reached, plotted against the left side of equation 2, and the curve 230 associated with the fitting model derived above as the right side of equation 2. Note that some dots are not visible as they are plotted on top of each other. The thirty-one ablation results are depicted in four groups of horizontally spaced dots, at 60V, 70V, 80V and 95V, which correspond respectively to the value of 70 degrees C./$V_M^2$ (on the vertical axis 210) of 0.0194, 0.0143, 0.0109 and 0.078 degrees C. per volt.

The first group 240 at 0.0194 is centered around approximately 100 ms with a range of about 50-160 milliseconds.

The second group 250 at 0.0143 is at approximately 25 milliseconds.

The third group 260 at 0.0109 is centered around approximately 35 milliseconds with a arrange of about 20-45 milliseconds The fourth group 270 is centered around approximately 22 milliseconds with a range of 10-35 milliseconds The fitting curve 230 intersects the first group 240 at approximately 107 milliseconds, the second group 250 at approximately 47 milliseconds, the third group 260 at approximately 30 milliseconds, and the fourth group 270 at approximately 19 milliseconds. The value of TT was determined to be 40.4±4.8 milliseconds, and C was determined to be (5.19±0.39)×10$^{-7}$ for this fitting curve 230.

The measurements were repeated using different r.f. treatment electrode diameters of 100 and 400 micron. Analysis of all the data showed C to be linearly correlated to the r.f. treatment electrode radius R according to equation 3:

$$C = R \cdot K$$

wherein:
  C is the constant in equations 1 and 2;
  R is the radius of the maximum extent of the circular r.f. treatment electrode 10 in millimeters through the skin contact plane, and
  K is a constant, per millimeter-millijoule, determined here to be 0.38±0.03 mm$^{-1}$ mJ$^{-1}$.

For programming the treatment settings determiner 30, it is more convenient to re-arrange the equations such that the user may select the skin damage onset factor J, as the user is principally interested in operating in one of the three treatment regimes depicted in FIG. 2. The damage onset factor J is associated with the end of the desired treatment regime, i.e. the point at which damage to the skin is considered undesired.

The treatment settings determiner 30 may be programmed to determine the treatment settings according to equation 4:

$$J = K \cdot R \cdot TT \cdot P_M \cdot (1 - \exp(-T_D/TT)),$$

wherein:
  J is a skin damage onset factor associated with a transition between a desired treatment result and an undesired treatment result;
  K is the constant, per millimeter-millijoule, from equation 4, dependent on skin tissue thermal and dielectric properties;
  R is a radius of the r.f. treatment electrode 10 in the contact plane in millimeters;
  TT is a thermal time constant of skin tissue in milliseconds;
  $P_M$ is the r.f. power associated with the r.f. treatment signal in Watts, equal to $V_M^2/Z_O$, wherein $V_M$ is the voltage of the r.f. treatment signal; and
  $T_D$ is the treatment duration in milliseconds.

The treatment device may be programmed to determine the power ($P_M$) associated with the r.f. treatment signal according to one or more of the following formulas:

$$P_M = I_M^2 \cdot Z_O, \text{ or}$$

$$P_M = V_M^2/Z_O,$$

wherein:
  $I_M$ is the electrical current of the r.f. treatment signal in Amperes;
  $Z_O$ is the initial skin impedance in Ohms; and
  $V_M$ is the voltage of the r.f. treatment signal in Volts.

The predictive power of the treatment settings determiner 30 based on equation 4 was validated using measurements, obtained by repeated r.f. treatment, on ex vivo skin samples at different r.f. treatment voltages $V_M$ of 51 V, 60 V, 70 V, and 80 V for a constant r.f. treatment duration $T_D$ of 50 ms. Further measurements were made for different r.f. treatment durations $T_D$ of 35 ms, 57 ms, 86 ms and 128 ms at a constant r.f. treatment voltage $V_M$ of 60 V. The non-invasive treatment device used for this validation comprised an r.f. treatment electrode 10 having a diameter of 200 micron surrounded by an annular return electrode having an inner radius of 3 mm in the plane of the skin contact areas of the electrodes.

For each setting, ten r.f. treatments were applied, and the actual number of skin tissue coagulation lesions, identified using NTBC staining of histological sections, were counted and converted to a probability of coagulation, i.e. the ratio between number of observed lesions and the number of treatments. Non-ablative skin tissue coagulation is the preferred treatment result for the use of the invention and is associated with the central treatment regime 170 depicted in FIG. 2.

For the validation, the initial skin impedance ($Z_O$) was recorded prior to each treatment. The value of J was then determined for each r.f. treatment voltage $V_M$, r.f. treatment duration $T_D$, and initial skin impedance $Z_O$. The ten values for each validation setting were averaged to determine an impedance-determined probability based on equation 4. The probability of a thermal event, e.g. a coagulation event, is related to the value of J by a sigmoid function. For example, at low values of J, the probability is close to zero, whereas high values of J show a coagulation probability of 100%. The critical point in the probability curve close to a value of 100% is associated with the peak value of J, which is 1 for coagulation. These impedance-determined probabilities were then compared to the actual lesion probability.

Figure 4:
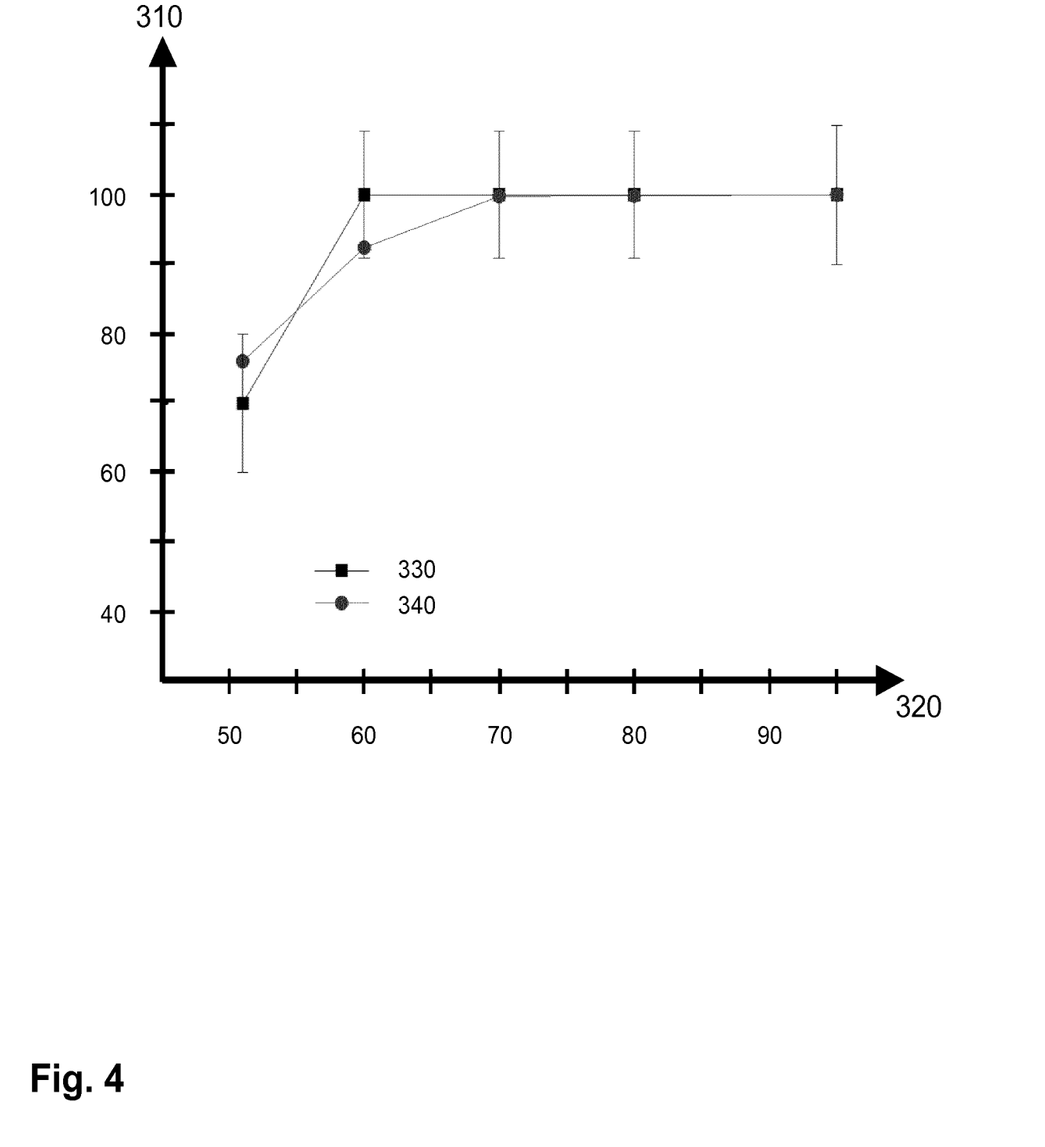
FIG. 4 depicts validation results for different r.f. treatment voltages and a fixed treatment duration.

FIG. 4 depicts the validation results for different r.f. voltages and a fixed treatment duration. The horizontal axis 320 represents the r.f. treatment voltage $V_M$ in volts from 50 to 90 Volts, and the vertical axis 310 represents the probability in percent (%) of coagulation lesions from 30 to 110 percent (%). The actual lesion probability 330 is plotted using squares, and at:

51 Volts it amounts to approximately 70±10%
60 Volts it amounts to approximately 100±10%
70 Volts it amounts to approximately 100±10%
80 Volts it amounts to approximately 100±10%.

The impedance-determined probability 340 is plotted using circles, and at:

51 Volts it amounts to approximately 76%
60 Volts it amounts to approximately 92%
70 Volts it amounts to approximately 100%
80 Volts it amounts to approximately 100%

The impedance-predicted probability 340 corresponds to a high degree with the actual lesion probability 330.

Figure 5:
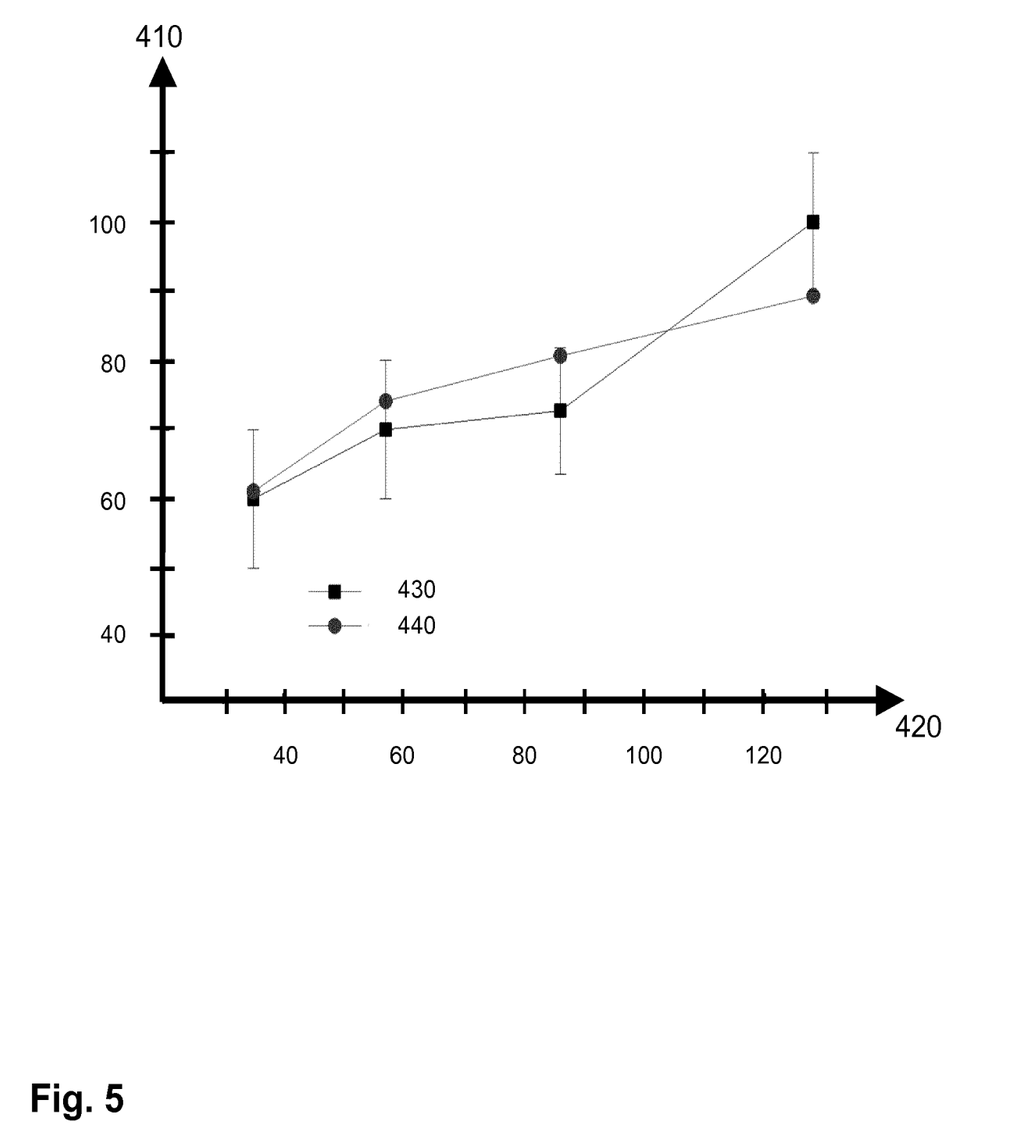
FIG. 5 depicts validation results for a fixed r.f. treatment voltage and different r.f. treatment durations.

FIG. 5 depicts the validation results for a fixed r.f. treatment voltage and different r.f. treatment durations. The horizontal axis 420 represents the r.f. treatment duration $T_D$ in milliseconds from 0 to 130 milliseconds, and the vertical axis 410 represents the probability in percent (%) of coagulation lesions from 30 to 110 percent (%). The actual lesion probability 430 is plotted using squares, and at:

35 milliseconds it amounts to approximately 60±10%
57 milliseconds it amounts to approximately 70±10%
86 milliseconds it amounts to approximately 73±10%
128 milliseconds it amounts to approximately 100±10%.

The impedance-determined probability 440 is plotted using circles, and at:

35 milliseconds it amounts to approximately 62%
57 milliseconds it amounts to approximately 75%
86 milliseconds it amounts to approximately 81%
128 milliseconds it amounts to approximately 90%

The impedance-determined probability 440 corresponds to a high degree with the actual lesion probability 430.

Based on these measurements, it was found that:
setting the skin damage onset factor J to 1±0.3 reliably predicted the onset of coagulation, i.e. the treatment result that corresponds with the transition 140 from the heating regime 160 to the coagulation regime 170 as depicted in FIG. 2;
setting the skin damage onset factor J to 1.7±0.5 reliably predicted the onset of ablation, i.e. the treatment result that corresponds with the transition 150 from the coagulation regime 170 to the ablation regime 180 as depicted in FIG. 2.

Accordingly, the device is configured and programmed to operate in the desired treatment regime by setting or predetermining the treatment duration $T_D$, before the actual treatment, so as to be less than or equal to the treatment time associated with the transition from a desired treatment result to an undesired treatment result. The non-invasive treatment device 100 also takes into account many factors which normally affect r.f. treatment, such as humidity, body location, differences between subjects, because the initial skin impedance ($Z_O$) is measured through the approximate path of the r.f. treatment signal in the skin. The other parameters affecting the efficacy and treatment duration, and which relate to the operating parameters of the device, such as r.f. voltage, r.f. treatment current and electrode dimensions, may be fixed or made variable in a single device, as their effects on treatment duration may be predicted.

The dimension of the r.f. treatment electrode in the skin contact plane may be made variable by means of a suitable mechanical construction, such as selectable electrode tips, or by providing an array or a concentric arrangement of electrode elements which are appropriately connected to or disconnected from the r.f. generator.

Given the existence of this surprisingly high degree of predictability based upon the initial skin impedance measurement ($Z_O$), the skilled person may further refine the calculations of the constants for the operating parameters of a particular device and/or particular use.

The controller 25 may further be programmed to prevent the r.f. generator 20 from being activated to apply the treatment signal if the initial skin impedance is greater than a predetermined upper limit or smaller than a predetermined lower limit, to prevent potentially unsafe operation.

Although it is not essential, the treatment device 100 may perform the skin impedance measurements also during the actual skin treatment. In such an embodiment, the values of the measured actual skin impedance may be used to modify the predicted treatment duration $T_D$, or to stop the treatment in case the skin impedance unexpectedly becomes higher than a predetermined further upper limit or lower than a predetermined further lower limit, for example due to incorrect operation of the device by the user or an unexpected skin moisture content.

Although single electrodes are depicted and described, a plurality of electrodes or arrays of electrodes, either for the treatment or the return electrode, may be provided for fractional treatment. Such a plurality of electrodes may be operated individually, in groups, or all together. A plurality of impedance measurement circuits 35 and a plurality of treatment settings determiners 30 may also be advantageous.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer.

The word "module" should not be interpreted to mean that the functionality and hardware are distinguishable in the device. It is used to indicate a functionality that the device comprises, and in practice different "modules" may use some or all of the same hardware and optical components.

In the device claim enumerating several means, several of these means may be embodied by one and the same item of hardware. The mere fact that certain measures are recited in mutually different dependent claims does not indicate that a combination of these measures cannot be used to advantage.

OVERVIEW OF REFERENCE NUMBERS 10 r.f. treatment electrode
15 inner region of the skin where r.f. treatment current may flow
20 r.f. generator
25 r.f. controller
30 treatment settings determiner
35 impedance measurement circuit
40 return electrode
60 skin
90 treatment target (in inner region of the skin)
100 r.f. treatment device
110 (FIG. 2) vertical axis=impedance measured during r.f. treatment in ohm
120 (FIG. 2) horizontal axis=r.f. treatment duration ($T_D$) in milliseconds
130 (FIG. 2) impedance profile 130 during treatment
140 (FIG. 2) transition 140 from the heating regime 160 to the coagulation regime 170
150 (FIG. 2) transition 150 from the coagulation regime 170 to the ablation regime 180
160 (FIG. 2) heating treatment regime
170 (FIG. 2) coagulation treatment regime
180 (FIG. 2) ablation treatment regime
210 (FIG. 3) vertical axis=70/$V_M^2$
220 (FIG. 3) horizontal axis=treatment duration ($T_D$) until onset of skin ablation
230 (FIG. 3) the curve associated with the fitting model
240 (FIG. 3) the first group of measurements at $V_M$=60V
250 (FIG. 3) the first group of measurements at $V_M$=70V
260 (FIG. 3) the first group of measurements at $V_M$=80V
270 (FIG. 3) the first group of measurements at $V_M$=95V
310 (FIG. 4) vertical axis=probability in percent of coagulation lesions
320 (FIG. 4) horizontal axis=r.f. treatment voltage ($V_M$) in volts
330 (FIG. 4) actual lesion probability (square markers)
340 (FIG. 4) impedance-determined probability (circle markers)
410 (FIG. 5) vertical axis=probability in percent of coagulation lesions
420 (FIG. 5) horizontal axis=r.f. treatment duration ($T_D$) in milliseconds
430 (FIG. 5) actual lesion probability (square markers)
440 (FIG. 5) impedance-determined probability (circle markers)
Co constant dependent on skin tissue thermal properties
K constant, per millimeter-millijoule, dependent on skin tissue thermal and dielectric properties
R radius of the r.f. treatment electrode (10) in millimeters
TT thermal time constant of skin tissue in milliseconds
$P_M$ power associated with the r.f. treatment signal in Watts, an r.f. electrical parameter
$T_D$ treatment duration in milliseconds
$I_M$ electrical current in the r.f. treatment signal in Amperes, an r.f. electrical parameter
$Z_O$ initial skin impedance in Ohms
$V_M$ voltage of the r.f. treatment signal in Volts, an r.f. electrical parameter
T temperature in degrees C. at time t (in milliseconds) during the treatment
t time during the treatment (in milliseconds) when the temperature T is determined.

The invention claimed is:

1. A non-invasive skin treatment device for heating an inner region of skin using radio-frequency (r.f.) electrical current, the skin treatment device comprising:
    an r.f. treatment electrode, having a first skin contact area for contacting an outer surface of the skin, configured to allow r.f. electrical current to pass through the inner region below the outer surface of the skin;
    a return electrode, having a second skin contact area for contacting the outer surface of the skin adjacent the r.f. treatment electrode, configured to allow the r.f. electrical current to pass through the inner region;
    an r.f. generator configured to apply, during treatment, an r.f. treatment signal between the r.f. treatment electrode and the return electrode through the inner region for heating the inner region;
    an impedance measurement circuit configured to measure a skin impedance between the r.f. treatment electrode and the return electrode;
    a treatment settings determiner configured to determine:
        treatment settings associated with the r.f. treatment signal, and
        a skin damage onset factor, associated with a transition between the desired treatment result and an undesired treatment result, depending on an r.f. voltage associated with the r.f. treatment signal and the treatment duration; and
    a controller programmed to activate the impedance measurement circuit, before the r.f. generator applies the r.f. treatment signal, to measure an initial skin impedance ($Z_O$) between the r.f. treatment electrode and the return electrode, and to predict occurrence of a thermal event at the transition between the desired treatment result and the undesired treatment result according to the skin damage onset factor,
    wherein the treatment settings determiner determines the treatment settings depending on the measured initial skin impedance ($Z_O$) and on a dimension of the r.f. treatment electrode in a contact plane defined by the first skin contact area, the treatment settings comprising at least a treatment duration ($T_D$) associated with a desired treatment result and an r.f. electrical parameter associated with the r.f. treatment signal;
    wherein the controller is further programmed to:
        activate the treatment settings determiner to determine the treatment settings after activating the impedance measurement circuit to measure the initial skin impedance;
        configure the r.f. generator to provide the r.f. treatment signal according to the treatment settings; and
        activate the r.f. generator to apply the r.f. treatment signal to the inner region for the treatment duration ($T_D$).

2. The skin treatment device according to claim 1, wherein the treatment duration ($T_D$) is associated with a transition in the inner region from a desired treatment result to an undesired treatment result.

3. The skin treatment device according to claim 2, wherein the undesired treatment result is associated with coagulation or ablation within the inner region.

4. The skin treatment device according to claim 1, wherein a maximum dimension of the r.f. treatment electrode in the contact plane of the r.f. treatment electrode is less than or equal to 2 mm.

5. The skin treatment device according to claim 1, wherein the r.f. electrical parameter associated with the r.f. treatment signal is one or more of the following:
   $I_M$, being an electrical current of the r.f. treatment signal in Amperes;
   $V_M$, being a voltage of the r.f. treatment signal in Volts; and
   $P_M$, being a power associated with the r.f. treatment signal in Watts.

6. The skin treatment device according to claim 1, wherein the controller is further programmed such that the controller prevents the r.f. generator from being activated to apply the treatment signal to the inner region if the measured initial skin impedance ($Z_O$) is greater than a predetermined upper limit or smaller than a predetermined lower limit.

7. The skin treatment device according to claim 1, wherein:
   the impedance measurement circuit is further configured to measure, during treatment, an actual skin impedance between the r.f. treatment electrode and the return electrode; and
   the controller is further programmed to interrupt, during treatment, the r.f. generator to prevent it from applying the r.f. treatment signal to the inner region when the actual skin impedance is greater than a predetermined further upper limit or smaller than a predetermined further lower limit.

8. The skin treatment device according to claim 1, wherein the second skin contact area of the return electrode is larger than the first skin contact area of the r.f. treatment electrode.

9. The skin treatment device according to claim 1, wherein the second skin contact area of the return electrode is at least five times larger than the first skin contact area of the r.f. treatment electrode.

10. The skin treatment device according to claim 1, wherein a location of a treatment target in the inner region relative to the r.f. treatment electrode is determined in part by a relative size of the second skin contact area to the first skin contact area.

11. A non-invasive skin treatment device for heating an inner region of skin using radio-frequency (r.f.) electrical current, the skin treatment device comprising:
   an r.f. treatment electrode, having a skin contact area defining a contact plane, configured to allow r.f. electrical current to pass through an outer surface of the skin and through the inner region;
   a return electrode configured to allow the r.f. electrical current to pass through the outer surface of the skin and through the inner region;
   an r.f. generator configured to apply, during treatment, an r.f. treatment signal between the r.f. treatment electrode and the return electrode through the inner region for heating the inner region;
   an impedance measurement circuit configured to measure a skin impedance between the r.f. treatment electrode and the return electrode;
   a treatment settings determiner configured to determine treatment settings associated with the r.f. treatment signal; and
   a controller programmed to activate the impedance measurement circuit, before the r.f. generator applies the r.f. treatment signal, and to measure an initial skin impedance between the r.f. treatment electrode and the return electrode,
   wherein the treatment settings determiner determines the treatment settings depending on the measured initial skin impedance (Zo) and on a dimension of the r.f. treatment electrode in the contact plane, the treatment settings comprising at least a treatment duration ($T_D$) associated with a desired treatment result and an r.f. electrical parameter associated with the r.f. treatment signal, and further determines:

$$J = K \cdot R \cdot TT \cdot P_M \cdot (1 - \exp(-T_D/TT)),$$

wherein:
   J is a skin damage onset factor associated with a transition between the desired treatment result and an undesired treatment result;
   K is a constant, per millimeter-millijoule, dependent on skin tissue thermal and dielectric properties;
   R is a radius of the r.f. treatment electrode in the contact plane in millimeters;
   TT is a thermal time constant of skin tissue in milliseconds;
   $P_M$ is an r.f. power associated with the r.f. treatment signal in watts, equal to $V_M^2/Z_O$, wherein $V_M$ is voltage of the r.f. treatment signal; and
   $T_D$ is the treatment duration in milliseconds, and
   wherein the controller is further programmed to:
   activate the treatment settings determiner to determine the treatment settings after activating the impedance measurement circuit to measure the initial skin impedance;
   configure the r.f. generator to provide the r.f. treatment signal according to the treatment settings; and
   activate the r.f. generator to apply the r.f. treatment signal to the inner region for the treatment duration.

12. The skin treatment device according to claim 11, wherein K is equal to 0.38±0.03 $mm^{-1}$ $mJ^{-1}$.

13. The skin treatment device according to claim 11, wherein TT is equal to 40.4 ± 4.8 milliseconds.

14. The skin treatment device according to claim 11, wherein the skin damage onset factor (J) is one or more of the following:
   J=1±0.3, when a transition within the inner region from a desired treatment result to an undesired treatment result is associated with onset of non-ablative coagulation damage; or
   J=1.7±0.5, when a transition within the inner region from a desired treatment result to an undesired treatment result is associated with onset of ablative damage.

15. A non-invasive skin treatment device for heating a target within an inner region of skin using radio-frequency (r.f.) electrical current, the skin treatment device comprising:
   an r.f. treatment electrode having a first skin contact area, defining a contact plane, for contacting an outer surface of the skin;
   a return electrode, having a second skin contact area for contacting the outer surface of the skin adjacent the r.f. treatment electrode;
   an r.f. generator configured to apply, before treatment, an r.f. impedance signal to the r.f. treatment electrode passing through the inner region to the return electrode for measuring an initial skin impedance, and subsequently to apply, during treatment, an r.f. treatment signal to the r.f. treatment electrode passing through the inner region to the return electrode for heating the target in the inner region;

an impedance measurement circuit configured to measure skin impedance between the r.f. treatment electrode and the return electrode when the r.f. impedance signal is applied to the r.f. treatment electrode;

a treatment settings determiner configured to determine:
  treatment settings of the skin treatment device depending on the measured initial skin impedance and on a dimension of the first skin contact area of the r.f. treatment electrode, the treatment settings comprising at least a treatment duration associated with a desired treatment result and an r.f. electrical parameter associated with the r.f. treatment signal; and
  a skin damage onset factor, associated with a transition between the desired treatment result and an undesired treatment result, depending on an r.f. voltage associated with the r.f. treatment signal and the treatment duration; and a controller programmed to configure the r.f. generator to provide the r.f. treatment signal according to the treatment settings; to activate the r.f. generator to apply the r.f. treatment signal to the inner region for the treatment duration; and to predict occurrence of a thermal event at the transition between the desired treatment result and the undesired treatment result according to the skin damage onset factor.

16. The skin treatment device according to claim 15, wherein the second skin contact area of the return electrode is larger than the first skin contact area of the r.f. treatment electrode.

17. The skin treatment device according to claim 15, wherein the second skin contact area of the return electrode is at least five times larger than the first skin contact area of the r.f. treatment electrode.

18. The skin treatment device according to claim 15, wherein a location of a treatment target in the inner region relative to the r.f. treatment electrode is determined in part by a relative size of the second skin contact area to the first skin contact area.

19. The skin treatment device according to claim 15, wherein the second skin contact area is in substantially a same plane as the first skin contact area when contacting the outer surface of the skin.

20. The skin treatment device according to claim 15, wherein the transition between the desired treatment result and the undesired treatment result comprises a transition from a heating regime to a coagulation regime or a transition from the coagulation regime to an ablation regime.

* * * * *